United States Patent [19]

Eisert et al.

[11] Patent Number: 4,548,499
[45] Date of Patent: Oct. 22, 1985

[54] ARRANGEMENT FOR MEASURING FLUORESCENCE POLARIZATION

[75] Inventors: Wolfgang Eisert, Hanover; Wolfgang Beisker, Garbsen, both of Fed. Rep. of Germany

[73] Assignee: Gesellschaft für Strahlen- und Umweltforschung mbH, Neuherberg, Fed. Rep. of Germany

[21] Appl. No.: 470,282

[22] Filed: Feb. 28, 1983

[30] Foreign Application Priority Data

Mar. 12, 1982 [DE] Fed. Rep. of Germany ....... 3208919

[51] Int. Cl.$^4$ ........................................... G01N 21/64
[52] U.S. Cl. ................. 356/318; 250/461.2; 356/73
[58] Field of Search ................. 356/73, 317, 318, 364, 356/366, 367, 369, 417; 250/458.1, 459.1, 461.1, 461.2

[56] References Cited

U.S. PATENT DOCUMENTS

| | | | |
|---|---|---|---|
| 4,122,348 | 10/1978 | Bruck | 250/461.2 |
| 4,203,670 | 5/1980 | Bromberg | 356/318 X |
| 4,352,558 | 10/1982 | Eisert | 250/461.2 X |

OTHER PUBLICATIONS

Biophysical Journal, vol. 31, Jul. 1980, pp. 97–112.

Primary Examiner—F. L. Evans
Attorney, Agent, or Firm—Spencer & Frank

[57] ABSTRACT

Arrangement for measuring the fluorescence polarization of cells or particles which are aligned individually along a flow stream illuminated by means of an illumination field wherein the cells are passed in succession through two light beams so as to excite fluorescence; the directions of polarization of the two excitation beams are perpendicular to one another; a pair of detector channels are provided to successively record the two polarization components of the fluorescence at both points of excitation; and an analysis system is provided which calculates the corrected degree of fluorescence for the individual cells from the measured values provided by the detector channels.

5 Claims, 6 Drawing Figures

ARRANGEMENT FOR MEASURING FLUORESCENCE POLARIZATION

BACKGROUND OF THE INVENTION

The present invention relates to an arrangement for measuring the fluorescence polarization of cells and particles which are individually aligned along a flow channel or stream and are illuminated by means of an illumination field.

When measuring the degree of fluorescence polarization, the fluorescent light is customarily measured either at 90° with a certain aperture angle or in the reverse direction (0°) over an angular range. To match the two detection channels (photodetector, electron amplifier) for parallel or vertically polarized fluorescent light, respectively, the polarization plane of the excitation light in a 90° arrangement is rotated in such a way that it lies in a plane defined by the two optical axes (excitation, detection). The two detection channels then receive nonpolarized light and can thus be set to the same sensitivity. For the actual measurement, the polarization vector is perpendicular to that plane. Since fluorescence is measured at a certain aperture angle, differences in the index of refraction of each cell and in the surrounding media play an important part in the attenuation of the individual polarization component during the measurement. Such matching should therefore take place in each of the cells to be measured in the 90° arrangement. This, however, is particularly impracticable if large quantities of cells or particles must be measured in sequence within a short time so as to record a distribution function, as this is the case, for example, in flowthrough cytometry.

In direct light fluorescence polarization measurements, a certain advantage resides in the fact that the influences of scattering of fluorescent light at internal structures on the measurement of the real degree of fluorescence polarization are of considerably less significance than in the 90° measurement. To match the two photodetectors, the direction of polarization of the exciting light is rotated here as well by 90° so that the detector for parallel polarized fluorescent light then receives the vertically polarized fluorescent light and vice versa. This method has the additional advantage that both individual measures contribute to an improvement in accuracy of the measurement of the degree of fluorescence polarization.

For rapid individual measurements in a large collection of cells, the collection is divided arbitrarily into one or a plurality of identically sized pairs of cell populations. For each pair, the degree of fluorescence polarization of the one half of the population having one excitation polarization is initially recorded in a histogram and then the excitation polarization is rotated by 90° and the degree of fluorescence polarization of the second half is recorded in a second histogram. If the detector channels are matched perfectly, and under the condition that both halves of the cell population exhibit the same behavior with respect to their degree of fluorescence polarization, the two polarization degree histograms must be identical. If they are not identical, which is observed in the majority of measurements, it is not necessary—in contradistinction to measurements in a 90° arrangement-13 to discard the values obtained; rather with the aid of a table-model calculator they can be computed to produce a corrected histogram for the degree of fluorescence polarization. (See: W. G. Eisert and W. Beisker, "Epi-Illumination Optical Design for Fluorescence Polarization Measurements in Flow Systems", Biophysics Journal, Vol 31, July 1980, pgs. 97–112).

All of these measuring methods require two individual measurements to match the measuring system and to make corrections at the individual specimen. This correction is impossible, as in the case of the 90° arrangement, or is possible only by matching before and controlling the matching after the measurement or, as in the case of direct light fluorescence polarization, by way of a statistical analysis of subpopulations.

SUMMARY OF THE INVENTION

It is therefore an object of the present invention to provide an arrangement which permits measurements of the polarization of fluorescent light in the same half area of excitation of fluorescence of individual particles with self-correction, with the cells or particles being brought individually and in succession through a measuring field where the degree of polarization of the fluorescence emission is measured in such a way that unavoidable fluctuations in the optical and electronic measuring system do not influence the measured value.

The above object is achieved according to the present invention by an arrangement for measuring the fluorescence polarization of cells which are aligned individually along a flow stream and are illuminated by means of an illumination field, which arrangement comprises means for producing first and second excitation beams of light with the direction of polarization of said excitation beams being perpendicular to one another, means for passing the cells whose fluorescence polarization is to be measured in succession through the first and second light beams at respective spaced points so as to excite fluorescence at each of these points, first and second detector means for successively detecting the respective two polarization components of the cell fluorescence at both spaced points of excitation, and analysis system means, responsive to the detected fluorescence values provided by the first and second detector means, for calculating the corrected degree of fluorescence for the individual cells from the detected values.

According to the preferred embodiment of the invention the two excitation light beams are simultaneously present, are focused at the two spaced points of excitation and are produced by splitting an unpolarized excitation beam or a polarized excitation beam whose polarization direction is set at an angle of 45° with respect to the polarization directions after splitting.

According to an alternative embodiment of the invention, the excitation takes place by means of a light beam whose polarization direction is rotated by 90° during the fluorescence excitation.

The correction of fluorescence polarization measurements of an individual specimen made according to the invention in a direct light arrangement by way of a further measurement with an excitation polarization that is rotated by 90°, thus provides, in principle, two possibilities:

(1) single beam system: while the cell is disposed in the measuring field, or moves through this field, respectively, the direction of polarization is rotated by 90° and a suitable electronic circuit records four measured values for this cell (2 parallel and 2 vertical intensity measurements). This possibility can be realized if the cells change slowly.

(2) Dual beam system: one specimen in a measuring field passes through two light beams in succession so as to excite fluorescence. The polarization directions of the exciting beams are here perpendicular to one another. The two polarization components of the fluorescence at both points of excitation are recorded in succession with the aid of a pair of detector channels. A special electronic analysis system calculates, from the four existing measured values, the corrected degree of fluorescence polarization before the next specimen enters the measuring field. When a nonpolarized excitation beam is split into its two polarization directions, these two directions can also be spatially separated into two parallel beams if a suitably cut calcide crystal is employed.

This arrangement according to the invention permits for the first time the measurement of changes in the degree of polarization of individual cells of a collection in rapid succession while maintaining an internal correction. The presently realized speed of electronic measured value processing and storage permits making a measurement approximately every 100 microseconds. If the measured data are stored in a list, this also permits the measurement of rapid changes in the degree of fluorescence polarization in a changing population. The calculation of the degree of polarization from four individual measurements further permits the numerical correction of the so-called aperture and refraction errors for every cell.

DETAILED DESCRIPTION OF THE PREFERRED EMBODIMENTS

Figure 1:
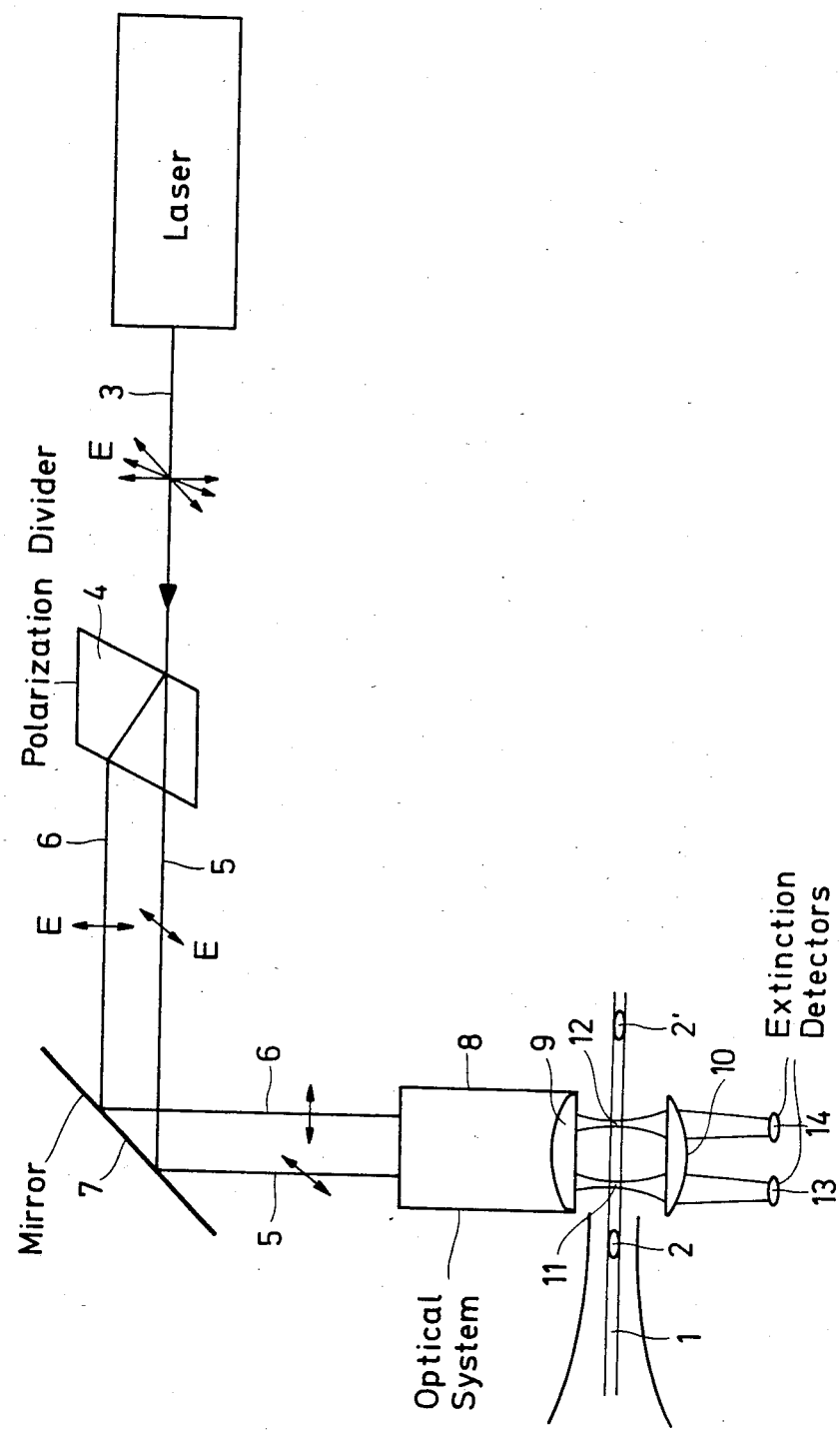
FIG. 1 is a schematic representation of a preferred embodiment of an irradiation system for individually aligned cells according to the invention.

Referring now to FIG. 1 there is shown a schematic representation of an irradiation system for cells 2, 2' . . . which are aligned individually in a flow system upon a stream 1. To irradiate the cells, a laser beam 3 is divided in a polarization divider 4 into two individual parallel beams 5 and 6 whose directions of polarization E and E' are perpendicular to one another as indicated by the double arrows. A deflection mirror 7 arranged at an angle to both beams 5 and 6 directs the two parallel beams 5 and 6 onto the optical system 8 which, in addition to optical devices for the detection of the fluorescence radiation to be described below, includes the lens 9. Lens 9 focuses the two beams 5 and 6, whose directions of polarization are perpendicular to one another, onto two regions 11 and 12, respectively, within the flow path 1 through which pass the individual cells 2, 2' and which regions have a constant known distance from one another. Extinction is measured by means of the two detectors 13 and 14 onto which the beams 5 and 6 are directed, respectively, by means of lens 10 disposed on the side of the stream 1 opposite from lens 9.

Figure 2:
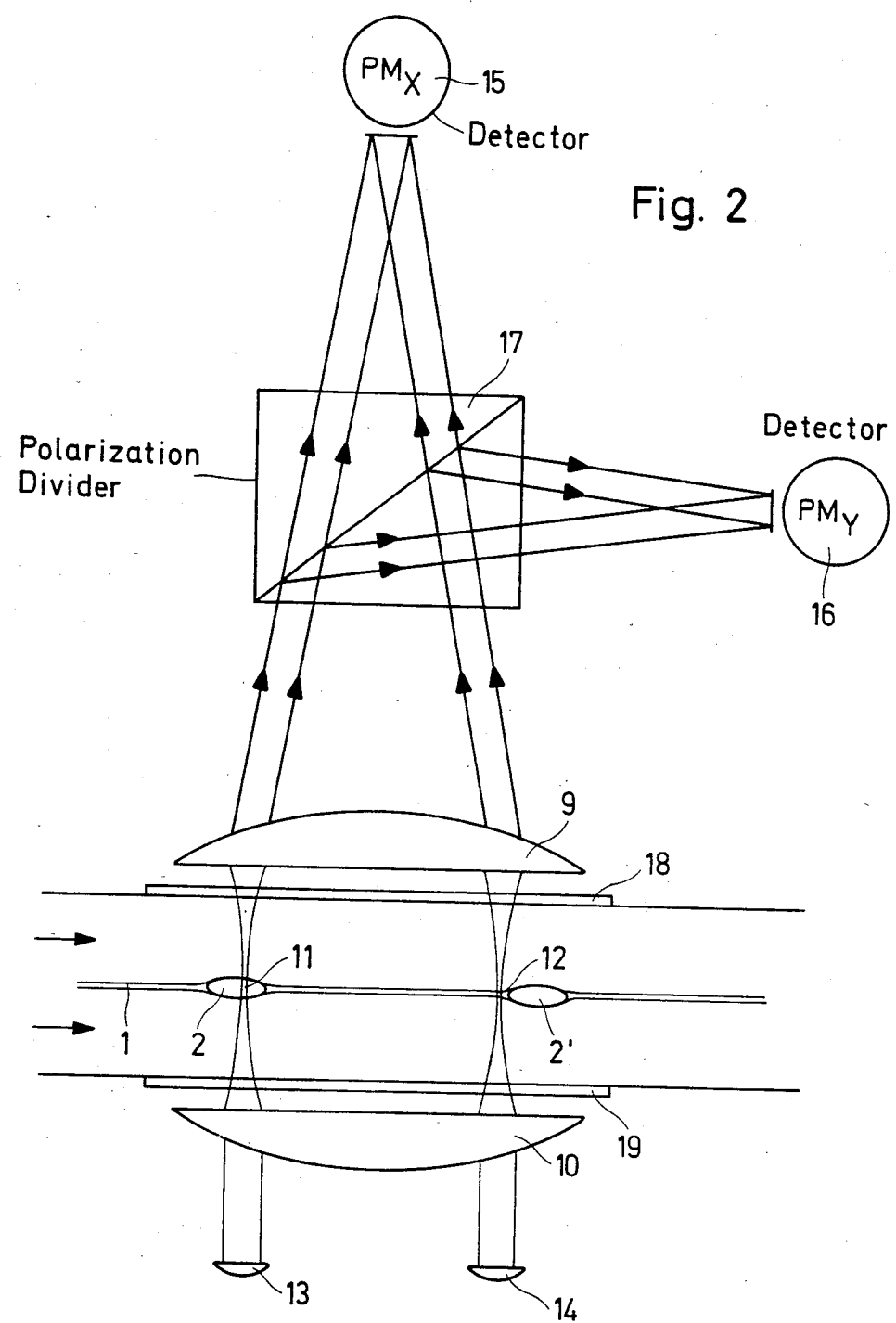
FIG. 2 is a schematic representation of a fluorescence detection system for the system of FIG. 1.

FIG. 2 shows the detector arrangement for the fluorescent raidiation emitted by cells 2 with only the passage of one cell 2 through the two focusing regions 11, 12 being under consideration here. For the sake of simplicity, the illumination or irradiating arrangement for emitting the two beams 5 and 6 as shown in FIG. 1 has been omitted; however, its beam paths lie on the same optical axis. The fluorescent radiation with perpendicular polarization directions and different intensity with respect to excitation regions 11 and 12, or the locus of cell 2 (one in region 11 and, after time $\Delta t$, in region 12) excited in regions 11, 12, of cells 2, 2' by the radiation 5 and 6 through the planar window 18, is measured simultaneously by detector or photomultiplier 15($PM_x$) for the x component and by detector or photomultiplier 16 ($PM_y$) for the y component. For this purpose, the fluorescence beams are again divided by a further polarization beam divider 17 according to their polarization direction and corresponding to the degree of polarization of the excited cell 2 so that two pairs of measured values from detectors 15 or 16, respectively, are recorded at intervals $\Delta t$ from one another, i.e. whenever they pass through the measuring locations 11 and 12. These four measured values then serve as self-correction for the fluorescence polarization measuring system of the present invention. As already shown in FIG. 1, extinction is measured by detectors 13 and 14 from the excitation or fluorescence radiation leaving the flow system through the likewise planar window 19.

Figure 3:
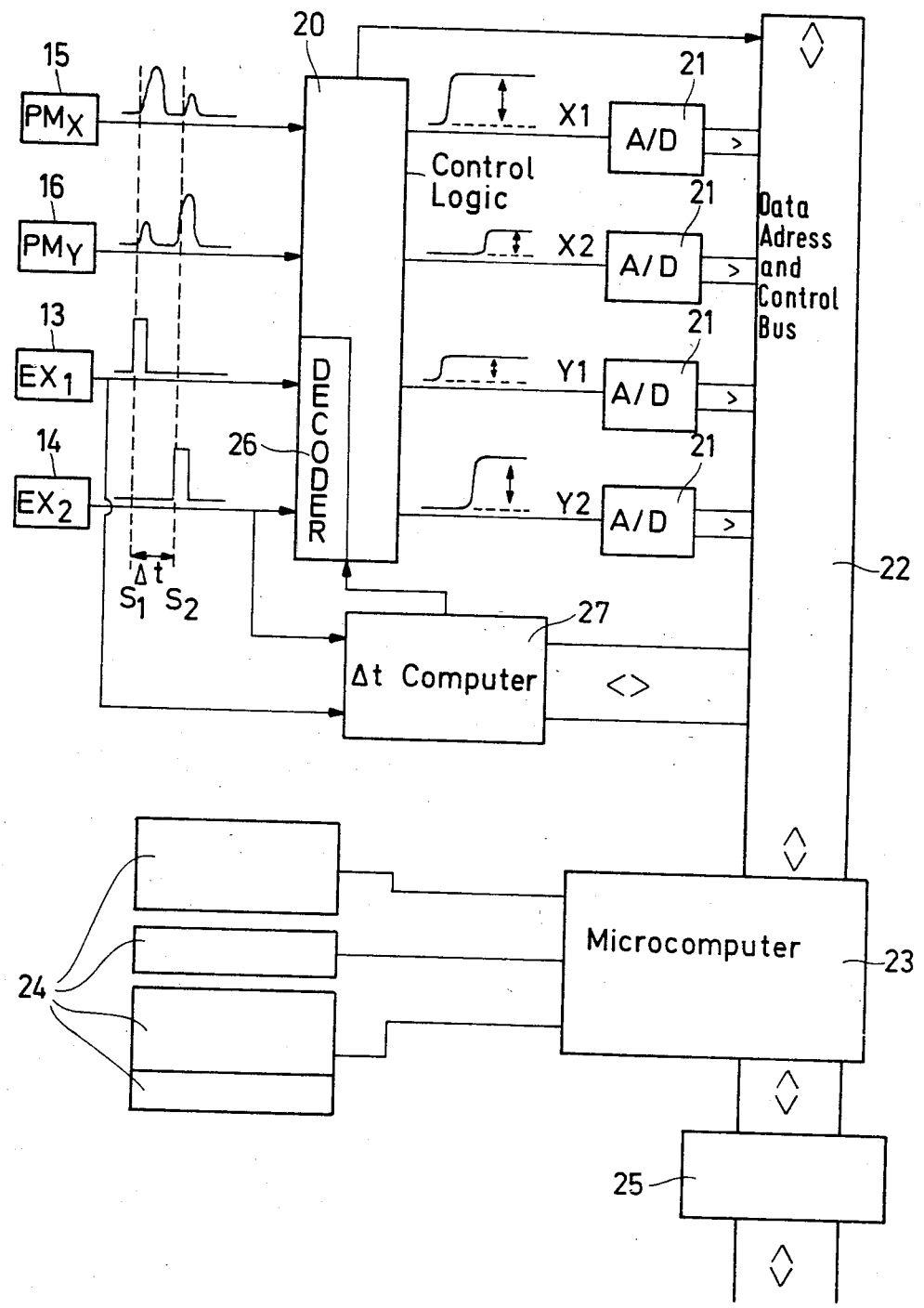
FIG. 3 is a block circuit diagram of a preferred embodiment of the calculating and control circuit for the self-correction of the fluorescence polarization measurements according to the invention.

The calculating and control circuit for this self-correction is shown in FIG. 3 in a schematic representation. The four measured or detected values, $2 \times PM_x$ and $2 \times PM_y$, from detectors 15 and 16, respectively, whose intensity and shape are plotted at time interval $\Delta t$ in FIG. 3, are fed via a maximum value decoder circuit incorporating a TTL control logic circuit 20 which emits respective amplitudes $X_1$, $X_2$, $Y_1$ and $Y_2$ to respective analog/digital converters 21. The output values of the analog/digital converters 21 are in turn fed via a data address and control bus 22, to a Z-80 type microcomputer 23. This microcomputer 23, with appropriate peripheral devices 24, 25 calculates the self-correction per cell 2 and serves as a data storage means unless immediate transfer via unit 25 to a minicomputer takes place. The measured extinction values $EX_1$ and $EX_2$ provided by detectors 13 and 14, respectively, are fed to a decoder 26, which is in communication with the calculating unit 23 via a $\Delta t$ computer 27 (start-stop), and to the computer 27. The position in time of extinction values $EX_1$ $EX_2$ with respect to the measured values $PM_x$ and $PM_y$ is also shown in FIG. 3.

Several peripheral devices 24, such as one or more floppy-disk units, a videoterminal and a plotter or a printer for data documentation can be connected to the microcomputer system 23. A serial or parallel interface 25 can be used for datatransfer to a large computer system.

Figure 4:
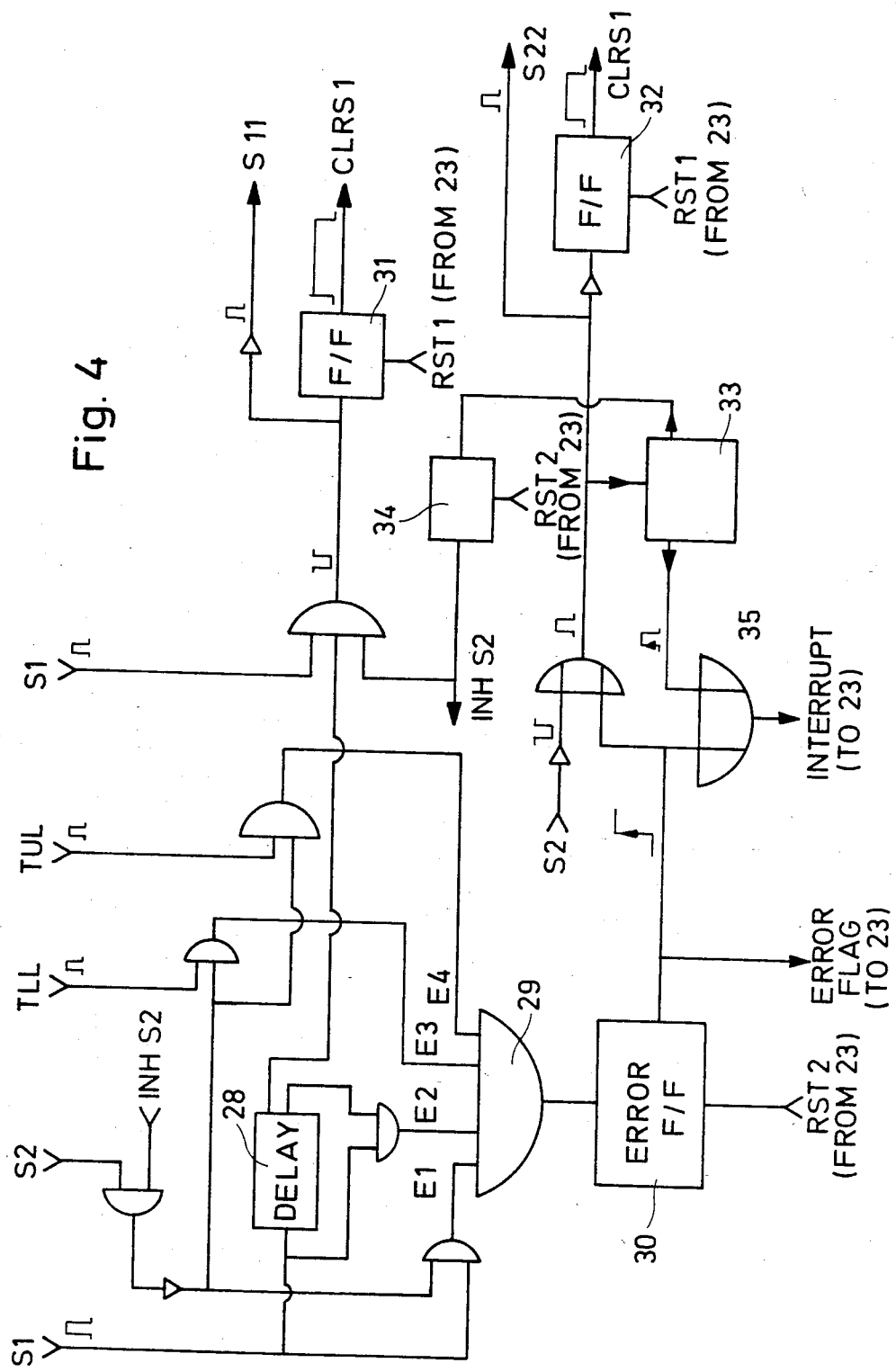
FIG. 4 is a logic circuit diagram of a pulse analysis circuit according to the invention for the circuit of FIG. 3.
Figure 5:
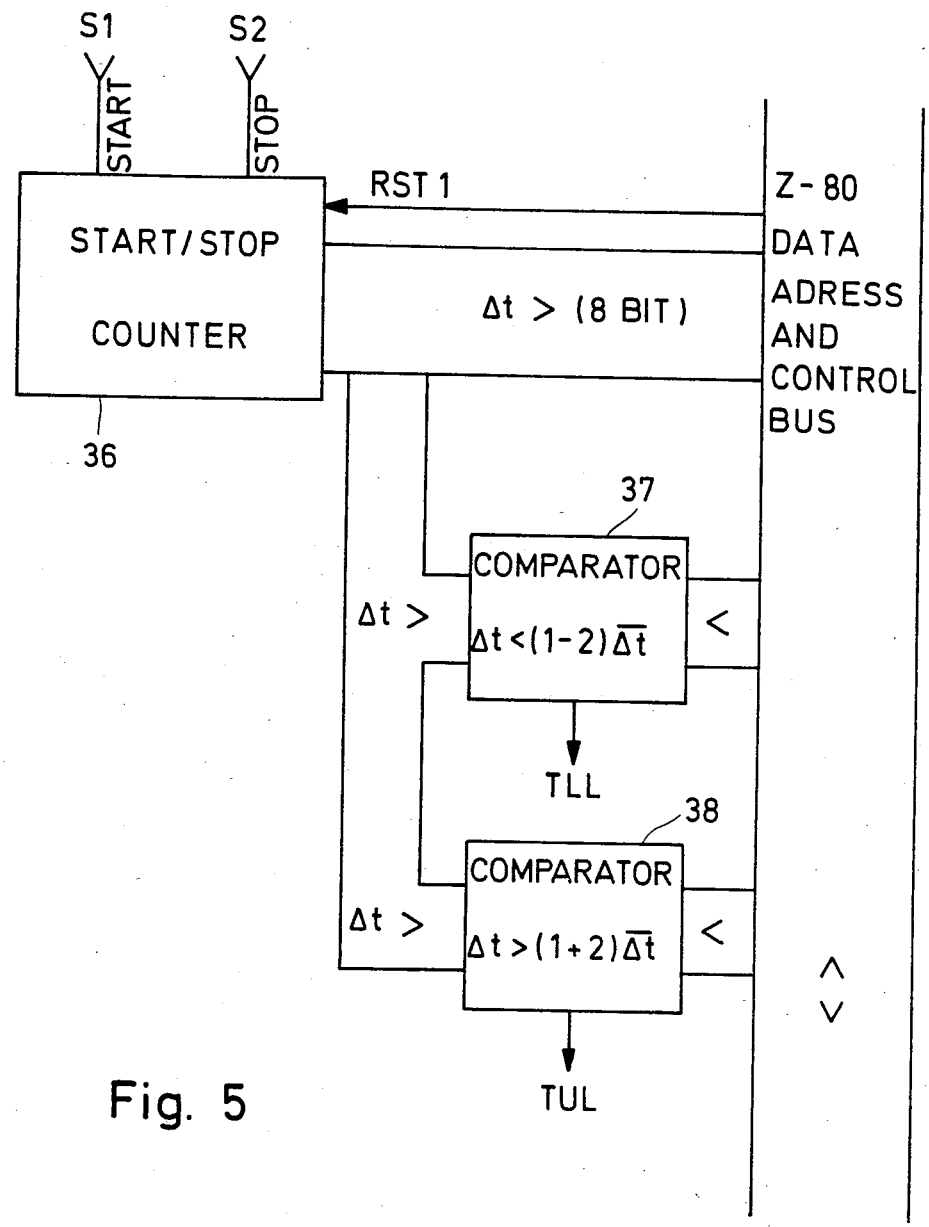
FIG. 5 is a block circuit diagram of the counter part of the time of flight processing unit.

FIG. 4 shows the processing of error conditions and the generation of the control signals S11, S22, CLRS1, CLRS2 for the control logic or analog processing unit 20, and FIG. 5 shows the block diagram of the counter part of the $\Delta t$ computer 27.

In the following text a differentiation made between $\Delta t$, which means the actual time of flight, and $\overline{\Delta t}$, which means the average time of flight calculated by computer 23 as an average of about 100 or more particles.

Figure 6:
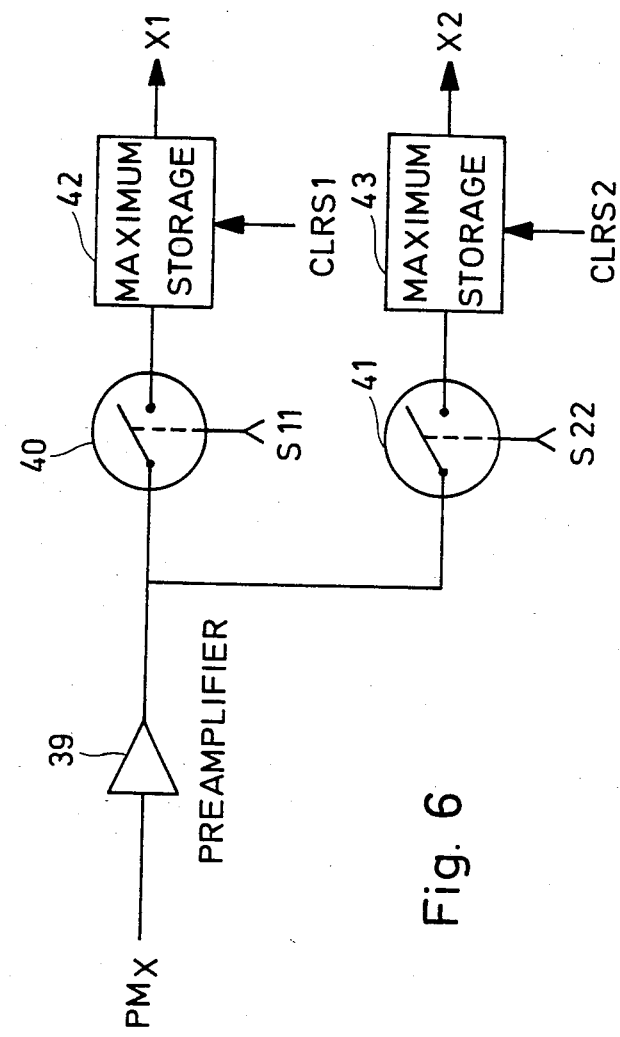
FIG. 6 is a block circuit diagram of the analog processing unit in FIG. 3 for one detector channel.

A start/stop counter 36 is started and stopped by the signals S1 and S2, generated by the extinction signals EX1 and EX2. The counting result Δt for each particle can be read from computer 23. The counter 36 can be reset by computer 23 via the RST1-signal. Two comparators 37, 38 are used for the generation of the signals TLL and TUL. A schematic representation of the analog signal processing in 20 is shown in FIG. 6 for one detector channel PMX.

After passing through a preamplifier 39, the signal is switched to two maximum storage devices 42, 43 which store the peak value of the signal pulses. With the analog switches 40 and 41, which are controled by the signals S11 and S22 coming from Δt computer 27, only signals during S1 or S2 are fed to the maximum storage devices 42, 43. Circuit 42 gets the signal of the first pulse during S1, and circuit 43 the signal during S2. This is to separate the two pulses coming drom PMX for input to two analog/digital converters (signal lines X1 and X2).

For channel PMY with the outputs Y1 and Y2 another circuit of the same design is used.

The respective signals, $S_1$ and $S_2$ of the light barriers, i.e. the signals produced by the extinction detector 13 and 14, respectively, (see FIGS. 3 and 4), as well as signals TLL and TUL, which are each produced in computer 27 from a comparison of the actual counter state Δt with the values $(1-\alpha)$ Δt and $(1+\alpha)$ Δt transmitted from computers 23 and 27, are fed to the pulse analysis unit according to FIG. 4.

The following applies for signals TLL and TUL:

TLL=1, if Δt<(1−α)Δt, and
TLL=0, otherwise;
TUL=1, if Δt≧(1−α)Δt, and
TUL=0, otherwise.

The further logic combination of signals $S_1$, $S_2$, TUL and TLL for the formation of control signals for the maximum decoders in circuit 20 is shown in FIG. 4. In this circuit, the block member 28 is a delay circuit which blocks the pulse analysis unit of FIG. 4 for a settable time interval (e.g. 40 μs) after each particle passage through the barrier providing signal $S_1$. AND-gate 29 combines the possible error conditions and sets the error flipflop 30 which can be interrogated by the microcomputer 23 via the output ERRORFLAG of flipflop 30. Flipflops 31 and 32 serve to store the pulse maxima for the signals $S_1$ and $S_2$, respectively, in the maximum decoder circuit and can be reset by microcomputer 23 via the respective reset inputs RST1. For each particle, the calculation is started in microcomputer 23 via the INTERRUPT signal produced by OR-gate 35 to prevent driving of the maximum decoders by a further particle passing through the first excitation region 11 with the calculation period.

At the same time, a monoflop 33 determines the length of the INTERRUPT-signal. Accordingly, an interrupt in computer 23 can be generated by an error condition or by a normal interrupt signal via gate 35.

Flipflop 34, which can be reset via computer by RST2, inhibits signals S1 and S2 during execution of the interrupt program in computer 23. RST2 is generated by computer 23 at the end of the interrupt program to prepare the system for registration of the next particle.

The signals S11 and S22 are connected with circuit 20 to switch the input signal from detectors 15 and 16 to the maximum storage devices 42 and 43. CLRS1 and CLRS2 are used to clear these storage devices 42 and 43. Decorder 26 is used to adapt the signals S11, S22, CLRS1, CLRS2 to the analog processing unit 20.

The following table explains the logic conditions of FIG. 4, when the Δt-computer 27 is driven with an interrupt program in computer 23. Columns (2) and (3) of the table give the possible error conditions, which have to be avoided by the Δt-computer 27 in cooperation with the interrupt program running in 23.

Column (2) of the table gives the condition E1∩E2 whereas column (3) gives the condition E3∩E4. At the output of gate 29 there will be a high level if any of the E1, E2, E3, E4 signals is going low. This generates an error condition in flipflop 30.

| (1) | (2) | (3) | (4) | (5) |
|---|---|---|---|---|
| Δt<(1 − α)Δt | 0 | 0 | (1− α)Δt | — |
| " | 0 | 1 | " | — |
| " | 1 | 0 | " | — |
| " | 1 | 1 | " | — |
| $\overline{Δt}(1 − α) < Δt < (1 + α)\overline{Δt}$ | 0 | 0 | Δt | yes |
| " | 0 | 1 | Δt | — |
| " | 1 | 0 | Δt | — |
| " | 1 | 1 | Δt | — |
| Δt>(1 + α)Δt | 0 | 0 | (1 + α)Δt | — |
| " | 0 | 1 | " | — |
| " | 1 | 0 | " | — |
| " | 1 | 1 | " | — |

In the above table, α is a freely selectable parameter for the width of the time window (e.g.=0.1).
Δt:time of flight
Δt:average time of flight (after calculation)

Explanations:

column (1): time of flight Δt of a cell or particle between leading edges of signals S1 and S2 (see FIG. 3)
column (2): simultaneous interruption of signals S1 and S2 (regions 11, 12) either by particles that are too long or by a second particle;
column (3): signal S1 indicates particles in region 11 within a time interval (which can be selected at will) after an interruption of the signal S1 by a particle;
column (4): time of flight for calculation of time average;
column (5): measurement of fluorescence polarization, for which there exists an additional condition that the fluorescence intensity of all four measuring channels must lie above a selectable level.

The intensity conditions are controled by the interrupt program running in computer 23.

It will be understood that the above description of the present invention is susceptible to various modifications, changes and adaptations, and the same are intended to be comprehended within the meaning and range of equivalents of the appended claims.

What is claimed is:

1. An arrangement for measuring the fluorescence polarization of cells which are aligned individually along a flow stream and illuminated by means of an illumination field, comprising in combination: means for producing first and second spaced excitation beams of light with the direction of polarization of said excitation beams being perpendicular to one another; means for passing the cells whose fluorescence polarization is to be measured in succession through said first and second light beams at respective spaced points so as to excite fluorescence at each of said points; first and second detector means for successively detecting the respective two polarization components of the cell fluorescence at said spaced points of excitation; and analysis system means, responsive to the detected fluorescence values provided by said first and second detector means, for calculating the corrected degree of fluorescence for the individual cells from said detected values.

2. An arrangement as defined in claim 1 wherein said means for producing first and second spaced excitation beams includes an unpolarized excitation light beam, and means for splitting said unpolarized excitation beam into said first and second excitation beams with perpendicular directions of polarization.

3. An arrangement as defined in claim 1 wherein said means for producing first and second spaced excitation beams includes a polarized excitation beam whose polarization direction is set at an angle of 45° with respect to the polarization directions of said first and second excitation beams, and means for splitting said polarized excitation beam into said first and second excitation beams.

4. An arrangement as defined in claim 1 further comprising a respective extinction detector means for detecting the extinction of the excitation beam by a cell disposed at each of said spaced points of excitation.

5. An arrangement as defined in claim 4 wherein said analysis system means is also responsive to the signals from said extinction detector means so as to determine the time of flight of a cell between said spaced points and the presence of a cell at each of said spaced points.

* * * * *